(12) United States Patent
Goodwin et al.

(10) Patent No.: US 6,988,547 B2
(45) Date of Patent: Jan. 24, 2006

(54) METHOD AND SYSTEM OF FLUID ANALYSIS AND CONTROL IN HYDROCARBON WELL

(75) Inventors: Anthony Robert Holmes Goodwin, Milton (GB); Kenneth Edward Stephenson, Newtown, CT (US); Gary Martin Oddie, St. Neots (GB); Robert Leonard Kleinberg, Ridgefield, CT (US); Douglas D. Griffin, Bethel, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 220 days.

(21) Appl. No.: 10/413,960

(22) Filed: Apr. 15, 2003

(65) Prior Publication Data

US 2004/0026076 A1 Feb. 12, 2004

Related U.S. Application Data

(60) Division of application No. 10/206,499, filed on Jul. 26, 2002, now Pat. No. 6,758,090, which is a continuation-in-part of application No. 09/459,054, filed on Dec. 10, 1999, now Pat. No. 6,490,916, which is a continuation-in-part of application No. 09/094,811, filed on Jun. 15, 1998, now Pat. No. 6,128,949.

(30) Foreign Application Priority Data

Dec. 23, 1998 (GB) .................................... 9828253

(51) Int. Cl.
*E21B 34/06* (2006.01)
*E21B 47/06* (2006.01)
*E21B 43/12* (2006.01)

(52) U.S. Cl. .................... 166/53; 166/66; 166/250.07; 166/250.15; 166/316

(58) Field of Classification Search ........... 166/250.15, 166/250.07, 53, 66, 316, 386
See application file for complete search history.

(56) References Cited

U.S. PATENT DOCUMENTS

2,380,082 A 7/1945 Sloan (Continued)

FOREIGN PATENT DOCUMENTS

DE 27 40 958 A1 3/1978

(Continued)

OTHER PUBLICATIONS

Abhijit et al, Measurement of phase behavior of hydrocarbon mixtures using fiber optical detection techniques, SPE 38845, Annual Technical Conference & Exhibition, San Antonio, Texas, Oct. 1997, pp 55-64.

(Continued)

*Primary Examiner*—Hoang Dang
(74) *Attorney, Agent, or Firm*—Jody Lynn DeStefanis; William L. Wang; Dale Gaudier

(57) ABSTRACT

A control system for a hydrocarbon well is also disclosed. A control valve system is used to control the flow of fluid being produced by the well. A real time sensor is provided downhole and is used to make real time measurements of phase characteristics of the fluid. A controller is used to control the valve system so as to reduce the risk of undesirable phase transitions in the fluid based on the real time measurements made by the sensor. The sensor includes an acoustic transducer configured to emit acoustic energy into the fluid at a level which causes a phase transition in the fluid. The controller determines the level of acoustic energy emitted into the fluid, and also determines the pressure associated with a phase transition using the level of emitted acoustic energy.

12 Claims, 11 Drawing Sheets

U.S. PATENT DOCUMENTS

| | | | |
|---|---|---|---|
| 4,092,858 A | 6/1978 | Edgerton | |
| 4,369,100 A | 1/1983 | Sawyer | |
| 4,659,218 A | 4/1987 | de Lasa et al. | |
| 4,782,695 A | 11/1988 | Glotin et al. | |
| 4,860,581 A | 8/1989 | Zimmerman et al. | |
| 5,024,110 A | 6/1991 | Doussiet et al. | |
| 5,097,698 A | 3/1992 | Wood et al. | |
| 5,329,811 A | 7/1994 | Schlutz et al. | |
| 5,473,939 A | 12/1995 | Leder et al. | |
| 5,587,525 A | 12/1996 | Shwe et al. | |
| 5,592,437 A | 1/1997 | Elliott | |
| 5,622,223 A | 4/1997 | Vasquez | |
| 5,635,631 A | 6/1997 | Yesudas et al. | |
| 5,636,631 A | 6/1997 | Waitz et al. | |
| 5,741,962 A | 4/1998 | Birchak et al. | |
| 5,799,733 A * | 9/1998 | Ringgenberg et al. | 166/264 |
| 6,128,949 A | 10/2000 | Kleinberg | |
| 6,176,312 B1 * | 1/2001 | Tubel et al. | 166/250.15 |
| 6,176,323 B1 | 1/2001 | Weirich et al. | |
| 6,182,756 B1 * | 2/2001 | Garcia et al. | 166/250.15 |
| 6,419,807 B1 * | 7/2002 | Davies et al. | 204/406 |
| 6,490,916 B1 | 12/2002 | Goodwin et al. | |
| 6,505,682 B2 * | 1/2003 | Brockman | 166/250.15 |
| 6,719,048 B1 * | 4/2004 | Ramos et al. | 166/250.15 |

FOREIGN PATENT DOCUMENTS

| | | |
|---|---|---|
| GB | 2 159 195 A | 11/1985 |
| GB | 2 302 114 A | 1/1997 |
| GB | 2 305 196 A | 4/1997 |
| GB | 2 309 471 A | 7/1997 |
| GB | 2 317 406 A | 3/1998 |
| GB | 2 338 563 A | 12/1999 |
| GB | 2 345 137 A | 6/2000 |
| SU | 802800 | 2/1981 |
| SU | 815619 | 3/1981 |
| SU | 901895 | 1/1982 |
| SU | 1206665 A | 1/1986 |
| WO | 87/06009 A1 | 10/1987 |
| WO | 96/24748 A1 | 8/1996 |
| WO | 96/24751 A1 | 8/1996 |

OTHER PUBLICATIONS

Adamson, Physical Chemistry of Surfaces, Third Edition, Chapter VIII, The formation of a new phase-nucleation and crystal growth, John Wiley & Sons, 1976, pp 372-384.

Amyx et al, Petroleum Reservoir Engineering, Physical Properties, McGraw-Hill Book Company, 1960, pp 220-229.

Blake-Coleman et al, Fluid density measurement using transducers based upon loudspeaker technology, Rev. Sci. Instrum, 62 (12), American Institute of Physics, Dec. 1991, pp 3068-3074.

Burfield et al, Vapor-liquid equilibria and dielectric constants for the helium-carbon dioxide system, AlChe Journal, vol. 16, No. 1, Jan. 1970, pp 97-100.

Chan, Dielectric constant of Ne near its liquid-vapor critical point, Physical Review B, vol. 21, No. 3, The American Physical Society, Feb. 1980, pp 1187-1193.

Chan et al, The dielectric constant in liquid and solid $^4$He*, Journal of Low Temperature Physics, vol. 26, Nos. 1/2, Plenum Publishing Corporation, 1977, pp 211-228.

Colgate et al, Acoustic resonance determination of sonic speed and the critical point for a typical retrograde gas condensate, Fluid Phase Equilibria, 79, Elesveir Science Publishers, 1992, pp 231-240.

Colgate et al, Sonic speed and critical point measurements in ethane by the acoustic resonance method, Fluid Phase Equilibria, 76, Elesveir Science Publishers, 1992, pp 175-185.

Daridon et al, Thermodynamic properties of liquid mixtures containing gas under pressure based on ultrasonic measurements, Fluid Phase Equilibria, 100, Elesveir Science Publishers, 1994, pp 269-282.

Daridon et al, Phase boundary measurement on a methane + decane + multi-paraffins system, Fluid Phase Equilibria, 117, Elesveir Science Publishers, 1996, pp 241-248.

de Loos et al, High pressure phase equilibria of interest for production and transport of natural gas and oil. (Abstract), Symposium on molecular thermodynamics for petroleum technology presented before the division of Petroleum Chemistry Incorporated 209th national meeting, American Chemical Society, Anaheim, CA, Apr. 1995. pp 169.

Doiron et al, Dielectric constant of $^3$He near liquid-vapor critical point, Physical Review B, vol. 17, No. 5, Mar. 1978, pp 2141-2146.

Fink, Time reversed acoustics, Physics Today, The American Institute of Physics, Mar. 1997, pp 34-40.

Fogh et al, Detection of high-pressure dew and bubble points using a microwave technique, Ind.Eng. Chem. Res., 28, American Chemical Society, 1989, pp 371-375.

Frorup et al, High pressure dew and bubble points from microwave measurements, Fluid Phase Equilibria, 52, Elesveir Science Publishers, 1989, pp 229-235.

Goodwin et al, Microwave detection of dew points: results for complex mixtures, J. Chem. Thermodynamics, 23, Academic Press Limited, 1991,pp 713-715.

Goodwin et al, Phase border and density determinations in the critical region of (carbon dioxide + ethane) determined from dielectric permittivity measurements, J. Chem. Thermodynamics, 29, Academic Press Limited, 1997, pp 1481-1494.

Goodwin et al, Reentrant radio-frequency resonator for automated phase-equilibria and dielectric measurements in fluids, Rev. Sci. Intrum., 67 (12), Dec. 1996, pp 4294-4303.

Hocken et al, Critical anomaly in the dielectric constant of a nonpolar pure fluid, Physical Review Letters, vol. 37, No. 15, Oct. 1976, pp 964-967.

Jamaluddin et al, A proactive approach to address solids (wax and asphaltene) precipitation during hydrocarbon production, SPE 49465, 8th Abu Dhabi International Petroleum Exhibition and Conference, Abu Dhabi, U.A.E., Oct. 1998, pp 1-17.

Kikani et al, Consistency check and reconciliation of PVT data from samples obtained with formation testers using EOS models, SPE 36743, Annual Technical Conference and Exhibition, Denver, Colorado, U.S.A., Oct. 1996, pp 615-622.

Maris et al, Negative pressures and cavitation in liquid helium, Physics Today, American Institute of Physics, Feb. 2000, pp 29-34.

Cavitation, Encyclopedia of Science Technology, McGraw-Hill, pp 317-320.

Michaels et al, Wireline fluid sampling, SPE 30610, Annual Technical Conference and Exhibition, Dallas, U.S.A., Oct. 1995, pp 871-878.

Montel, Phase equilibria needs for petroleum exploration and production industry, Fluid Phase Equilibria, 84, Elesveir Science Publishers, 1993, pp 343-367.

Rijkers et al, Measurements on the phase behavior of binary mixtures for modeling the condensation behavior of natural gas, Fluid Phase Equilibria, 72, Elesveir Science Publishers, 1992, pp 309-324.

Rogers et al, Microwave apparatus for phase transition studies of corrosive fluids to 1.7 kbar and 588k, Rev. Sci. Instrum., 56 (10), American Institute of Physics, Oct. 1985, pp 1907-1912.

Sever et al, A novel technique for rapid measurement of liquid-liquid-vapour equilibrium, Chemical Engineering Science, vol. 53, No. 14, Elsevier Science Ltd, 1998, pp 2587-2594.

Sirotyuk, Ultrasonic cavitation processes at elevated hydrostatic pressures, Soviet Physics—Acoustics, vol. 12, No. 2, Oct.-Dec. 1966, pp 199-204.

St-Arnaud et al, Application of the dielectric constant measurements to study the influence of the small quantities of water vapor on the compressibility factor of methane, International Journal of Thermophysics, vol. 13, No. 4, Plenum Publishing Corporation, 1992, pp 685-697.

Steiner et al, Visuelle und dakametrische bestimmung von phasengleichgewichten nichtmischbarer fliissigkeiten unter hochdruck, Zeitschrift fur Physikalische Chemie Neue Folge, Bd. 63, 1969, s 297-311.

Ziegler et al, Quartz sensor for automatic dew-point hygrometry, Sensors and Actuators, 11, Elsevier Sequoia, 1987, pp 37-44.

* cited by examiner

METHOD AND SYSTEM OF FLUID ANALYSIS AND CONTROL IN HYDROCARBON WELL

REFERENCE TO PRIOR APPLICATIONS

This is a divisional of U.S. patent application Ser. No. 10/206,499, which was filed Jul. 26, 2002 (now U.S. Pat. No. 6,758,090), which is a continuation-in-part of (1) U.S. patent application Ser. No. 09/459,054 (now U.S. Pat. No. 6,490,916), which was filed Dec. 10, 1999 and (2) U.S. patent application Ser. No. 09/094,811 (now U.S. Pat. No. 6,128,949), which was filed Jun. 15, 1998. U.S. patent application Ser. No. 09/459,054 claims priority to Great Britain Application No. 9828253.6, filed 23 Dec. 1998, now abandoned. All of these patent applications and their corresponding issued patents are incorporated by reference herein in their entireties.

FIELD OF THE INVENTION

The present invention relates to methods for downhole fluid analysis and real time production control of a well. More particularly, the invention relates to an improved method for analyzing thermodynamic phases of complex fluids downhole, and for using such analyses for real time process control.

BACKGROUND OF THE INVENTION

The control of fluid produced from each hydrocarbon reservoir zone can significantly improve the recovery factor. It can also minimize the production of undesirable fluids such as water and gas. In addition, such control could assist reservoir engineers with flood injections and chemical agent treatment.

Phase transitions play an important role in the producibility of oil or gas wells and their associated reservoirs. Fluid produced from an oil well will typically have a number of hydrocarbon components and, while these may coexist as liquid at the temperature and pressure of the reservoir rock, the lighter components may begin to evolve as gas as the wellbore and formation pressure is reduced. Such evolution of gas in the reservoir rock can seriously decrease the oil phase relative permeability and, ultimately, the fraction of oil that may be recovered. Knowledge of the bubble point is also useful in determining the composition of the hydrocarbon mixture in the reservoir. Similarly, in gas wells, heavier components may begin to condense as a liquid as gas is produced. Liquid in the pore spaces of a gas well will similarly reduce the permeability to gas. It is important to maintain either pure liquid or pure gaseous phase in the reservoir, depending on the type of well.

Reservoir performance calculations greatly benefit from a knowledge of the location of the fluid (p, T, x) pressure-temperature-composition phase transitions. At either reservoir or producing zone conditions the most significant phase borders are the formation of a liquid from a gas (dew point) and a gas from a liquid (bubble point). The phase behavior of black oils is usually dominated by the mole fraction of low molecular mass components, while for retrograde condensates the phase behavior is determined by mole fraction of high molecular mass components.

Fluid phase behavior also plays an important role in production engineering both down hole and at surface. It is often desirable to produce with the "drawdown", or decrease in wellbore pressure relative to the formation pressure, as large as possible to give the greatest production rate. Drawdown is limited, however, by the need to avoid phase changes in the fluid. In addition, failure to maintain a single phase in a horizontal well can create gas pockets that inhibit flow in production tubing. Both Reservoir and Production Engineers require the hydrocarbon phase be maintained homogeneous to optimize production while minimizing risk of reservoir damage.

Conventionally, there are several methods by which the phase behavior of reservoir fluids can be determined. However, none of these methods lend itself to real-time downhole sensors for in situ production control. Empirical correlations on laboratory data have been used to estimate phase borders. Alternatively, a bubble point can be estimated from a compositional analysis of fluid samples with an equation of state. Typically, samples collected down-hole and brought to the surface are liable to undergo both reversible and irreversible changes such as wax and asphaltene separation, that arise from temperature and pressure changes. In addition, the imperfect fluid transfer between sample apparatus and measuring apparatus alters the composition. Fluid thermophysical property analyses can be obtained at the well head, so reducing the time between sample collection and analysis. However, these approaches all require the handling and perhaps transportation of hazardous fluids. Finally, some properties of well fluids have been determined with a commercially available wireline tool down-hole, without removing the sample from the well. Commercial tools that can be used for this purpose are the Schlumberger Modular Formation Dynamics Tester (MDT) and the Western-Atlas Reservoir Characterization Instrument (RCI). Although in theory such devices could be used to provide, for a limited time period, real time in situ fluid properties, the sensors and methods are not sufficiently reliable for permanent or even semi-permanent operation.

None of the methods described above are performed on a routine basis and certainly never sufficiently often or rapidly to provide real-time data for process control. The only viable solution is permanent or semi-permanent down-hole monitoring.

SUMMARY OF THE INVENTION

Thus, it is an object of the invention to provide a method of accurately and efficiently determining thermophysical properties of both reservoir and produced fluid.

In particular, it is an object of the invention to provide a method of determining the phase border in a way that allows for improved real time process control and reservoir optimization with downhole chokes.

It is a further object of the invention to provide an improved method and system of controlling pressure in a well using real-time measurements of phase characteristics of fluid in the well.

It is a further object of the invention to provide measurements that minimize sample manipulation and transportation, thus ensure sample integrity.

It is a further object of this invention to provide a method and apparatus for accurately determining phase characteristics in a flow-by tool that does not require that a sample be captured in a closed volume.

It is a further object of this invention to provide a method and apparatus for determining phase characteristics in the well that does not require physical manipulation of the pressure of the fluid with moveable pistons, plungers or the like.

It is a further object of the invention to provide information on the phase transition pressure so that the flow control valves may be operated without incurring a phase transition in the reservoir or borehole.

As used herein, the term "real time" with respect to determining phase characteristics is defined as a frequency which allows accurate process control. In general, the higher the frequency of measurement the more accurate the control, since the phase boundary varies over time with variations in the fluid composition. However, in many situations monitoring the phase characteristics once per week will be more than sufficient to avoid the negative effects of producing too close to the phase boundary.

As used herein, the term "acoustic" is defined as including both the sonic and ultrasonic frequency ranges.

The preferred method of phase boundary detection involves using an acoustic transducer to create cavitation. In general, cavitation is considered impractical for fluid pressures above about 1 MPa and would appear impossible down hole. However, such generalities appear to have been formulated on the basis of measurements in water at pressures at least 1 MPa above phase separation with low-power cavitation sources. For a fluid close to the phase separation pressure, it has been found that localized pressure reductions created in acoustic waves will give rise to the evolution of transient cavitation bubbles at static pressures higher than the thermodynamic bubble point pressure.

The bubbles thus formed can be detected at the site where they are produced by monitoring the acoustic properties of the liquid. This is preferably done by monitoring the acoustic impedance of the acoustic transducers used to cavitate the fluid. At the first appearance of a bubble, even a transient bubble, the acoustic impedance mismatch between transducer and fluid is greatly altered. This in turn produces a change in the electrical impedance of the transducer.

Advantageously, according to the invention, a combination of measured static pressure and the detection of cavitation with an acoustic source generating a known acoustic pressure provides a determination of the bubble pressure. For permanent monitoring applications, this approach can be applied to both heterogeneous stratified and homogeneous mixed flow regimes when a sample is captured as a continuous hydrocarbon phase, and the volume of the secondary phase is determined by other means. Furthermore, the strategy can be used on flowing fluid, without recourse to sampling, within the completion tubing independent of production stream deviation in horizontal stratified flow provided the sensors are located in the hydrocarbon-continuous phase.

According to the invention, the acoustic pressure generated by the acoustic source can be determined from either calibration or a theoretical model based on finite element analysis and known physical properties of the transducers' environment. The semi-empirical model uses both the density and sound speed of the fluid. These properties can be determined with either the same or an independent transducer.

According to the invention, cavitation and the formation of bubbles can be determined by one or more of the following methods: passive emissions, transmission, reflection, sound speed, sound attenuation, optical, Doppler, backscattering, holography, microscopy, or Mie scattering. However the preferred method is by measuring the variance in impedance of an acoustic transducer.

According to one embodiment of the invention, a system and method of fluid analysis in a hydrocarbon borehole is provided for determining phase characteristics of a formation fluid. Acoustic energy is emitted into the fluid downhole at a level which causes a phase transition in the fluid. The pressure associated with the phase transition is then determined from the level of emitted acoustic energy. Advantageously, the determination of the phase transition pressure need not rely on mechanical means to substantially alter the volume of a sample of the fluid.

The acoustic energy is emitted by an acoustic transducer that can be installed either semi-permanently or permanently downhole in the well. The acoustic transducer can be contained in a flow-by tool that does not require that a sample be captured in a closed volume. Either the bubble point or the dew point can be detected. In the case of bubble point detection, the bubbles in the fluid can be detected by sensing variations in impedance of the acoustic transducer, and the level of emitted acoustic energy can determined by measuring the electrical energy used to drive the transducer.

According to another embodiment of the invention, a control system is provided for a hydrocarbon well. A control valve system is used to control the flow and the pressure of fluid being produced. A real time sensor is provided downhole and is used to make real time measurements of phase characteristics of the fluid. A controller is used to control the valve system so as to reduce the risk of undesirable phase transitions in the fluid based on the real time measurements made by the sensor.

The real time sensor can be installed permanently or semi permanently downhole in the well. The sensor preferably includes an acoustic transducer configured to emit acoustic energy into the fluid at a level which causes a phase transition in the fluid. The controller preferably determines the level of acoustic energy emitted into the fluid, and also determines the pressure associated with a phase transition using the level of emitted acoustic energy. Advantageously, the determination of the pressure associated with the phase transition need not rely on mechanical means to substantially alter the volume of a sample of the fluid. The phase transition detected can be the bubble point or the dew point. The phase transition pressure is preferably determined by sensing variations in impedance of the acoustic transducer which indicate the presence of bubbles in the fluid.

According to another embodiment of the invention, a system for determining phase characteristics of a hydrocarbon fluid sample in a bottle is provided. An acoustic transducer emits acoustic energy into the fluid at a level which causes a phase transition in the fluid. A controller is provided to determine the level of acoustic energy emitted into the fluid, and determine the pressure associated with the phase transition using the level of emitted acoustic energy. The system can be used to detect the bubble point or the dew point. The pressure associated with the phase transition is preferably determined by sensing variations in impedance of the acoustic transducer. The bottle preferably includes a hydraulically actuated piston to control the pressure of the fluid sample.

DETAILED DESCRIPTION OF INVENTION

Figure 1:
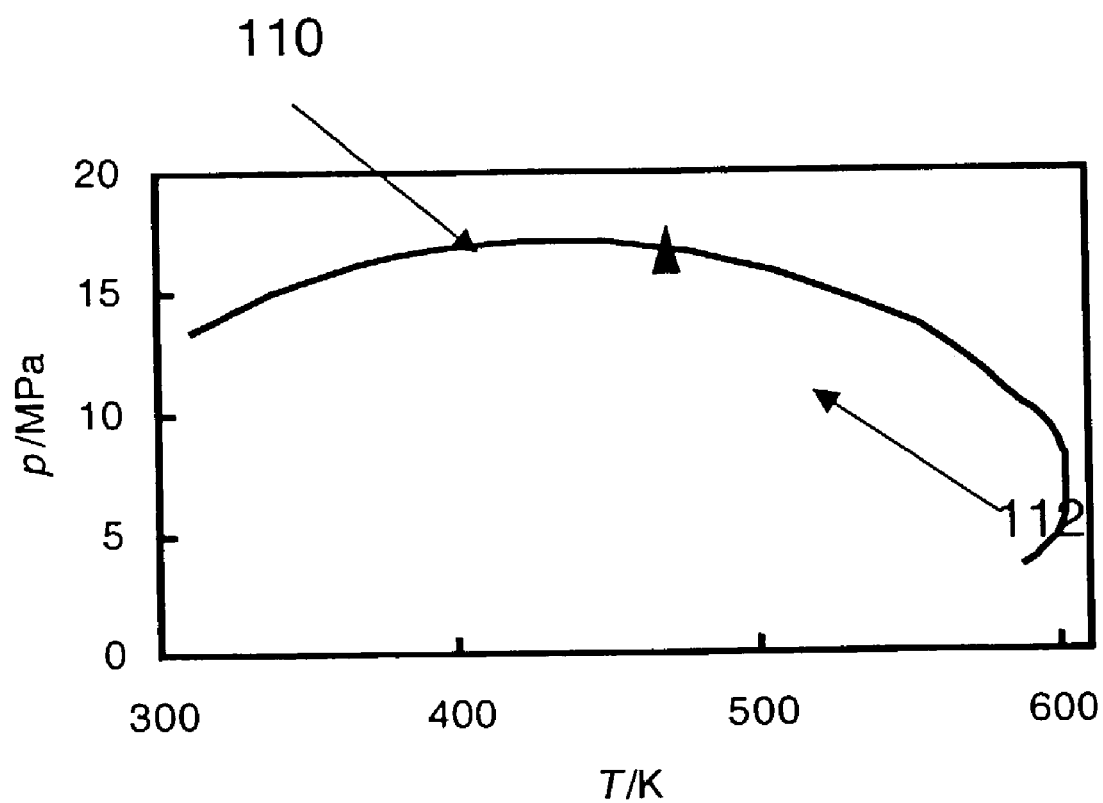
FIG. 1 shows an example plot in pressure and temperature of a phase border for an example fluid with composition defined in Table 1.

FIG. 1 shows an example plot in pressure and temperature of a phase border for an example fluid with composition shown in Table 1. The phase border shown in FIG. 1 was estimated using the program known as HASBRO. The triangle represents the critical condition. The portion of the curve on the left side of the triangle represents the bubble curve 110. The portion of the curve on the right side of the triangle represents the dew curve 112. Reservoir performance calculations greatly benefit from a knowledge of the location of the fluid (p, T, x) pressure-temperature-composition phase transitions. At either reservoir or producing zone conditions the most significant phase borders, shown in FIG. 1 for the mixture defined in table 1, are the formation of a liquid from a gas (dew point) and a gas from a liquid (bubble point). The phase behavior of black oils is dominated by the mole fraction of low molecular mass components, while for retrograde condensates the phase behavior is determined by mole fraction of high molecular mass components.

TABLE 1. Species i of mole fraction $x_i$ used to compute the phase envelope shown in FIG. 1.

| I | $X_i$ |
|---|---|
| $CH_4$ | 0.45 |
| $C_2H_6$ | 0.05 |
| $C_3H_8$ | 0.05 |
| $n-C_4H_{10}$ | 0.03 |
| $n-C_5H_{12}$ | 0.01 |
| $n-C_6H_{14}$ | 0.01 |
| $C_7+$ | 0.40 |

Figure 2:
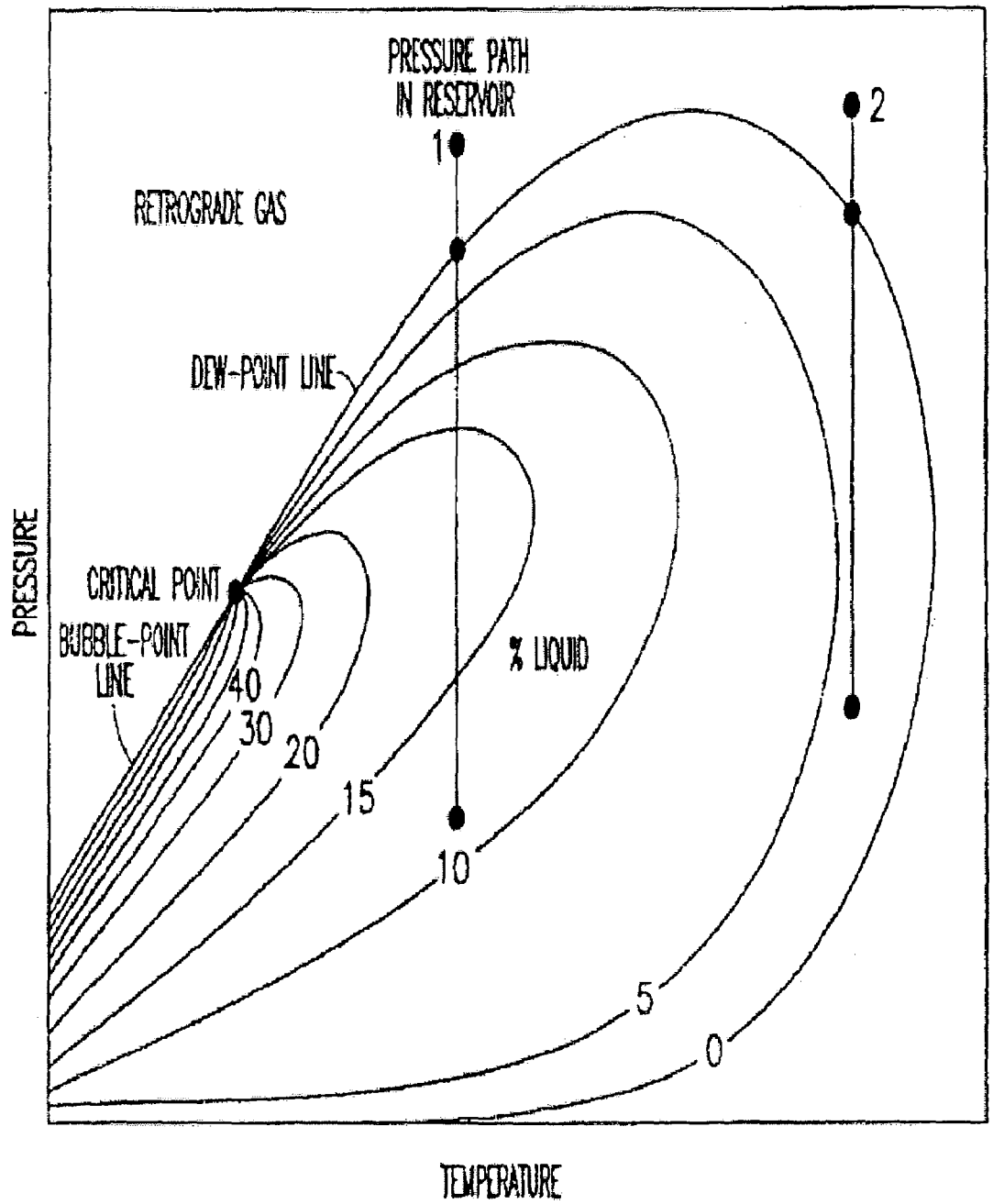
FIG. 2 depicts an exemplary graph of a phase diagram of a gas condensate reservoir.

FIG. 2 shows an example of a phase diagram of a gas condensate reservoir. The horizontal axis is temperature and the vertical axis is pressure. When a reservoir is first penetrated by a borehole, the reservoir is characterized by its original temperature and pressure. Two possible original states are shown, at Points 1 and 2. To bring the reservoir into production, the pressure is reduced at constant temperature. Thus, reservoir production is represented by movement down vertical lines in FIG. 2.

In order to maintain maximum permeability to hydrocarbon flow, it is important that only one fluid phase exist in the formation. This means that the pressure should remain above the Dew Point Line shown in FIG. 2 (and the bubble point line in FIG. 1). In the case of FIG. 2, above this line only gas exists; below the Dew Point Line liquid condenses, forming a two-phase mixture in the rock pores of the earth formation. The presence of two phases decreases permeability to fluid flow, and therefore reduces production rate.

The control of fluid produced from each reservoir zone can significantly improve the recovery factor. It can also, minimize the production of undesirable fluids such as water and gas. To do this, a series of sensors are normally used that determine pressure, temperature, flow rate, and physical properties of the reservoir fluid combined with one or more valves or chokes. In addition these sensors can be used to assist reservoir injection with water and chemical agents. Such an arrangement can be located in any part of the production system.

Figure 3:
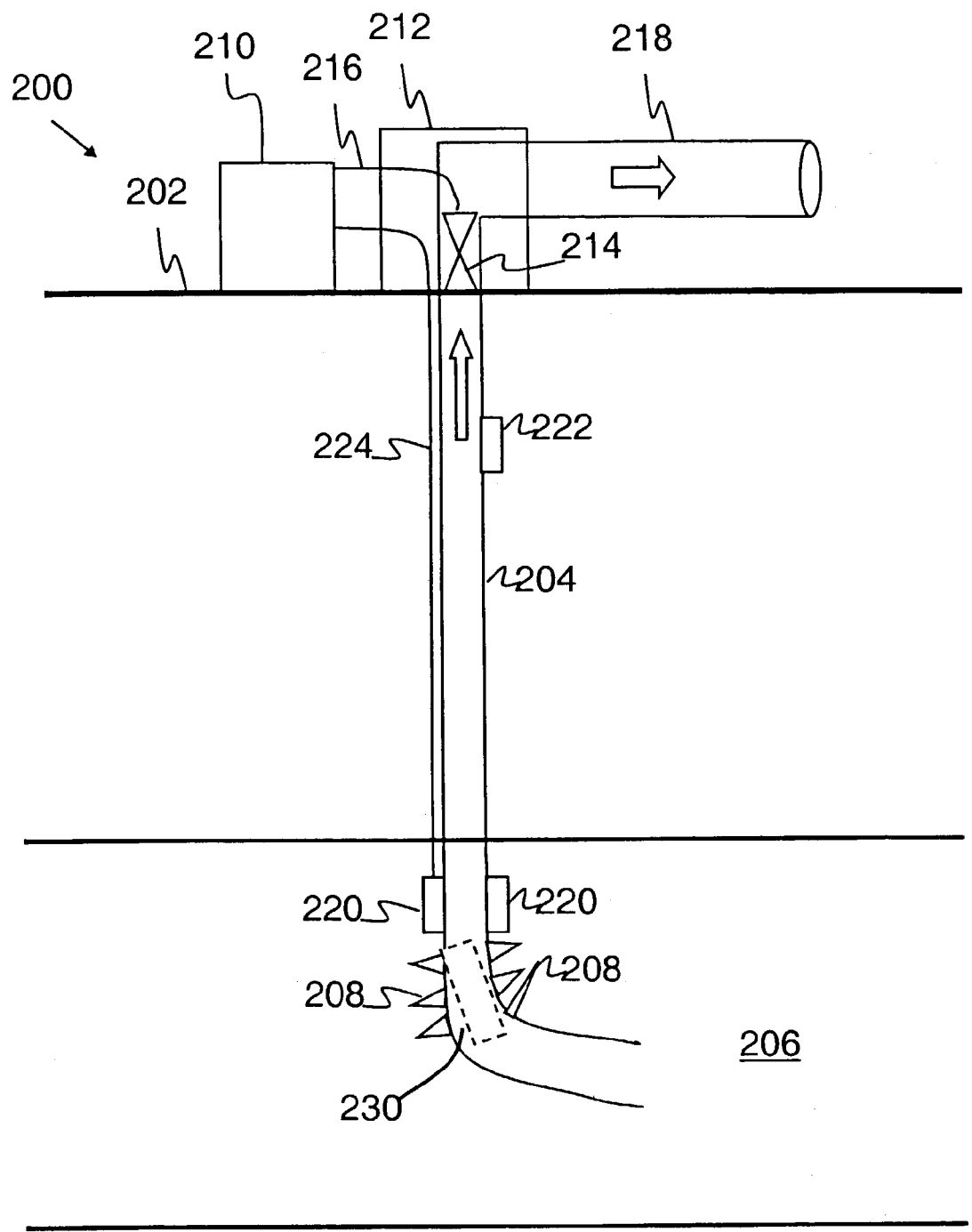
FIG. 3 shows a system for controlling pressure in a well based on real time measurements of the phase characteristics, according to a preferred embodiment of the invention.

FIG. 3 shows a system 200 for controlling pressure in a well based on real time measurements of the phase characteristics, according to a preferred embodiment of the invention. FIG. 3 shows system 200 in the case of a land surface completion, although the invention is equally applicable to sea bottom and sea surface completions. Production tubing 204 is shown penetrating land surface 202, and down through to the reservoir 206. A casing, not shown, would surround the production tubing and would be cemented in place. The well is perforated in the zone of the reservoir 206, as shown by arrows 208. Production fluid thus passes up through production tubing 204 and into the surface completion 212. Surface completion 212 comprises a flow control valve 214 adapted to restrict and control the flow of the production fluid. Downstream of the surface completion 212 is a transport pipeline 218.

According to the invention, sensors 220 are provided in the production zone for measuring the bubble point pressure. Sensors 220 are preferably installed either permanently, or semi-permanently. Although sensors 220 are shown in the production zone, in general the location of the sensor depends on what part of the process is being controlled. For example, if the concern is gas bubbles forming in the reservoir, the best location for the sensor is in or near to the production zone. On the other hand, if the concern is maintaining a fluid above the bubble point in some other part of the system, then the sensor should be placed in that region. For example, sensor 222 is shown at a different location. Additionally, in some situations a plurality of sensors should be deployed.

Controller 210 is located on the surface and communicates with valve 214 via cable 216. In some completions the controller 210 would be located within completion 212. For example, if completion 212 were a subsea completion, a protective dome could be provided inside of which could reside controller 210. Controller 210 comprises a computer and various controller hardware that is used to control the pressure of the well by setting the position of valve 214. As mentioned it is important the well pressure be maintained at a level that avoids gas bubble formation due to being too close to the bubble point. Sensors 220 and 222 communicate with controller 210 via cable 224. Sensors 220 and 222 contain sensors that can aid in the determination of the bubble point pressure for the production fluid. According to a preferred embodiment, sensors 220 comprise a bubble detection and formation package capable of real time operation, as will be described in further detail below. Sensors 220 may also comprise other detectors and sensors such as a pressure gauge for measuring the hydrostatic pressure. According to another embodiment of the invention which is described in further detail below, an intelligent completion system 230 is provided which communicates with sensors 220 and 222, and provides real time pressure control.

According to the invention, fluid composition is controlled based on input from the sensors 220 to control the opening of the flow control valve 214. Preferably, sensors 220 provide, amongst other data, measurement of ambient hydrostatic pressure and phase transition pressure. In the case of an oil well, the phase transition pressure of concern would be the bubble point pressure. These data are then used to adjust flow control valve 214 based on the requirement that the difference between phase transition pressure and ambient hydrostatic pressure is a desired value. The sensor measurements can also be used to control production flow rate at one or more locations in the well so that the produced flow rates are at desired values. These sensors might include the means for measurement of any one or several of the following physical properties of at least one phase of the fluid: density, viscosity, permittivity, sound speed, and phase border. In an oil well, system 200 can thus be used to accurately control the pressure at a level safely above the bubble pressure, but still be at a level consistent with optimum production.

This invention provides methods of determining downhole fluid thermophysical properties for real time monitoring which are used for process control of a hydrocarbon reservoir. The phase boundary, examples of which is shown in FIG. 1 and FIG. 2, is a key quantity for reservoir production optimization described above.

Various companies are now offering completions with flow meters and controllable valves. These "intelligent completion systems" (ICS) are intended to be installed at each producing zone to monitor, control, and optimize production. An example of and ICS 230 is depicted schematically in FIG. 3. Thus, according to another embodiment of the invention, information on the phase transition pressure is provided to ICS 230 so that flow control valves in ICS 230 may be operated without incurring a phase transition in the reservoir or borehole. It is not required that the actual thermodynamic phase transition pressure be measured (which will be different than the actual phase transition pressure as in, for example, supersaturated gases). According to the invention, from an operational point of view, it is sufficient to determine the pressure where free gas will be produced in oil wells, or liquid will be produced in gas wells.

In phase boundary measurements, depending on the density of nucleation sites, it is possible that the transition will be exhibited at a point that is not the true thermodynamic phase boundary; i.e., the fluid will be "supersaturated". This effect is reduced by the presence of a suitable disturbance such as acoustic shock, foreign body, and gas bubble or water droplet that will result in spontaneous phase separation at the true thermodynamic phase boundary. These disturbances are common in downhole fluids. Thus, one benefit of in-situ downhole measurement is that it is more likely to yield the true thermodynamic phase boundary. This might then be used in thermodynamic models for the reservoir.

According to the invention a particularly preferred method of fluid phase transition detection is a non-invasive and non-contacting approach that exploits acoustic cavitation. Cavitation advantageously avoids the need to vary the fluid pressure with a variable volume. Bubbles first form at the location where acoustic amplitude is greatest. Bubbles at the same place are readily detected by acoustic means, as described in further detail below. The bubble pressure can be determined from the difference between static pressure and acoustic pressure required to produce gas bubbles by cavitation. The cavitation threshold depends on a number of factors such as temperature, hydrostatic pressure, gas content, and frequency.

According to a preferred embodiment, the cavitation transducer can be both efficient and focused. There are many types of acoustic transducers that can be used for this purpose ranging from capacitive to piezoelectric devices. Whatever device is chosen, it should preferably be capable of operating at reservoir temperatures for years and at frequencies, typically less than 1 MHz, used to generate cavitation. The acoustic detection of cavitation preferably makes use of a transducer capable of operating over a wide frequency range. The frequencies of acoustic energy suitable for cavitation is believed to be in the range of 1 kHz and 50 kHz, with about 40 kHz being found suitable for certain applications. Additionally, the acoustic pressure range of the transducer should be high enough to include a safe pressure margin above the bubble point pressure. This will allow accurate control of the production pressure at a level which is safely above the bubble pressure of the production fluid. This pressure range will in general depend upon the fluid, location, and production requirements of the particular well.

The acoustic pressure applied to the fluid by the cavitation source can be determined from a combination of the applied power and physical characteristics of both transducer and surrounding media. In any case, the density and speed of sound in the fluid should be used. These properties can be determined from ancillary measurements or an equation of state given a fluid composition.

The preferred method of determining the pressure applied to the fluid is by using finite difference methods to solve the equations for acoustic propagation related to intensities of waves travelling through different media. The physical properties (such as speed of sound, viscosity and density) of the materials used to construct the transducer, the fluid surrounding it, and the physical dimensions are preferably used as inputs to a suitable program for finite element solutions to propagation of acoustic waves. It has been found that the program known as FEWaves is suitable for solving for the pressure in this application.

Figure 4:
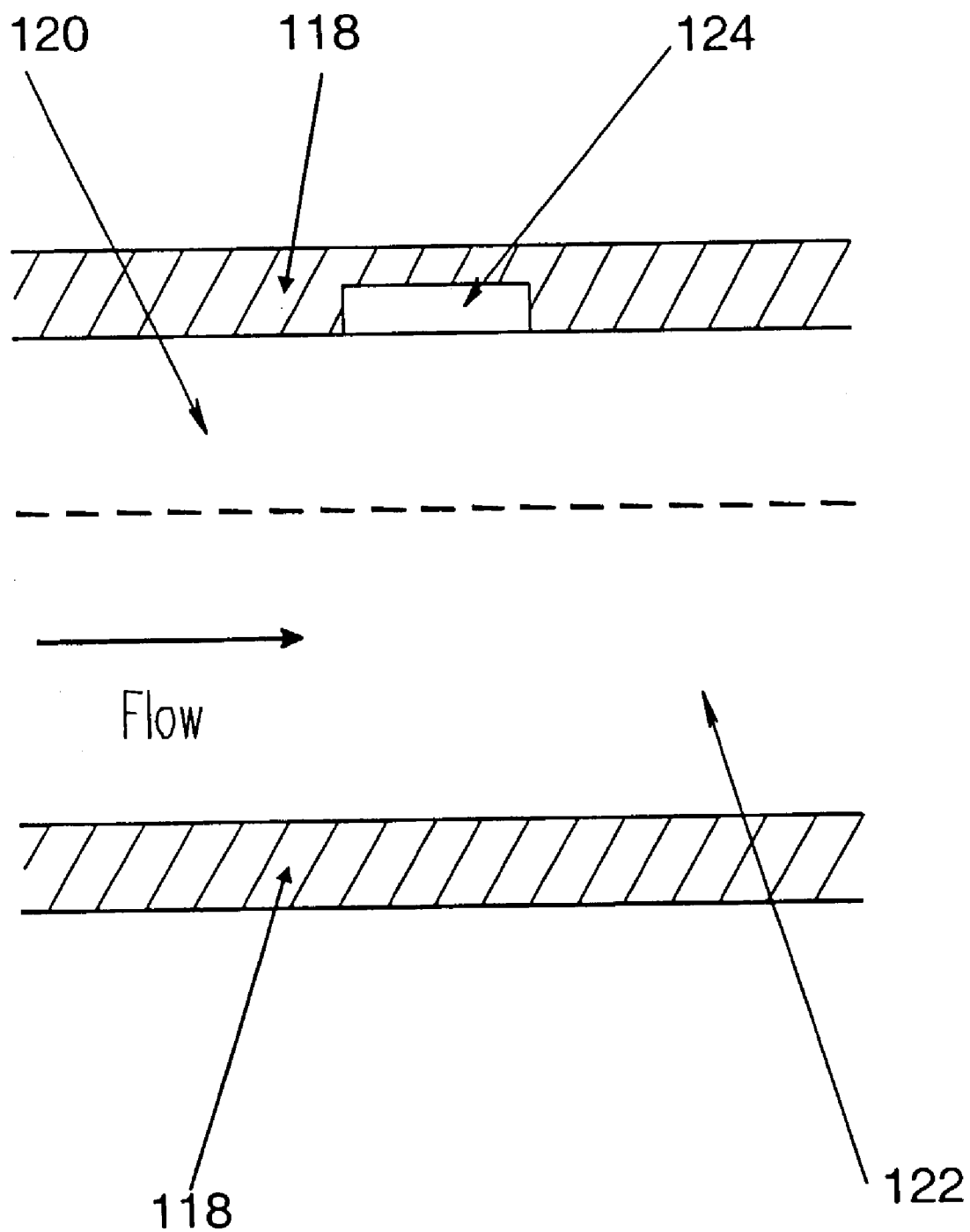
FIG. 4 shows a schematic of a bubble detection and formation system flush mounted on a horizontal casing according to a preferred embodiment of the invention.

FIG. 4 shows a schematic of a bubble detection and formation system flush mounted on a horizontal casing 118 according to a preferred embodiment of the invention. This embodiment is particularly suited for a horizontal stratified flow. The dashed line indicates the boundary between oil 120 and water 122. The bubble detection and formation system 124 is mounted flush on the horizontal casing. Deployed in such a manner, it does not interfere with flow of fluid through the flowline. It is also relatively immune from erosion and has no moving parts, which are important considerations in down hole tools. Advantageously, the sample is not captured but the measurements are performed on the flow-line fluid. If the fluid is heterogeneous and stratified, as shown in FIG. 4, then the bubble detection and formation system 124 should be located in the oil-continuous phase as shown in FIG. 4.

Figure 5:
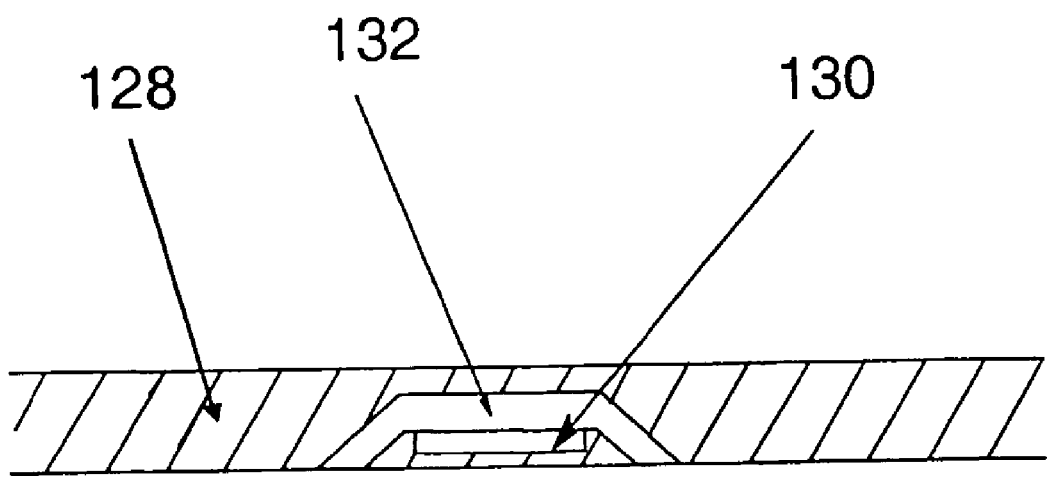
FIG. 5 shows a schematic of an intelligent completion system with a thermophysical property package according to a preferred embodiment of the invention.
Figure 5:
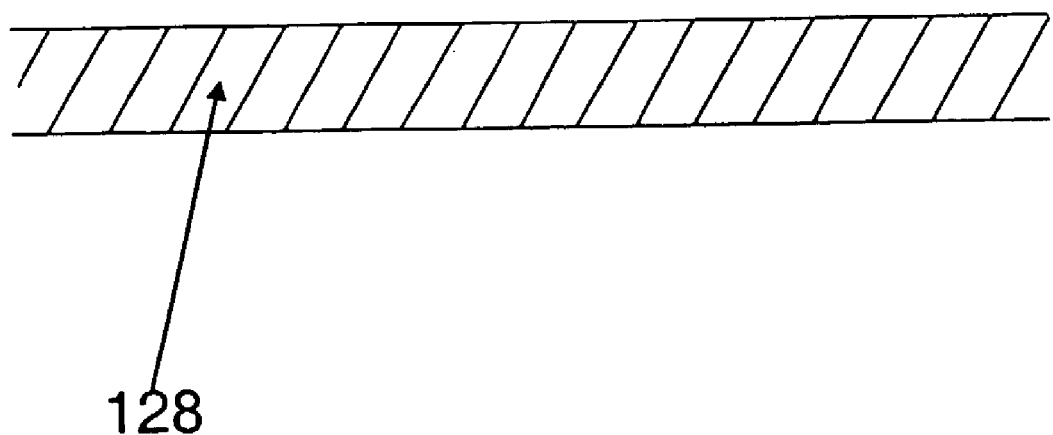

FIG. 5 shows a schematic of an intelligent completion system 128 with a thermophysical property package according to a preferred embodiment of the invention. FIG. 5 shows a version of the sensor applied to a sample capture system. The thermophysical property package 130 is provided within the fluid capture system 132. Preferably, the sample capture system should be designed so that it can be used in both homogeneous and heterogeneous (including stratified) flow regimes at any deviation.

Figure 6:
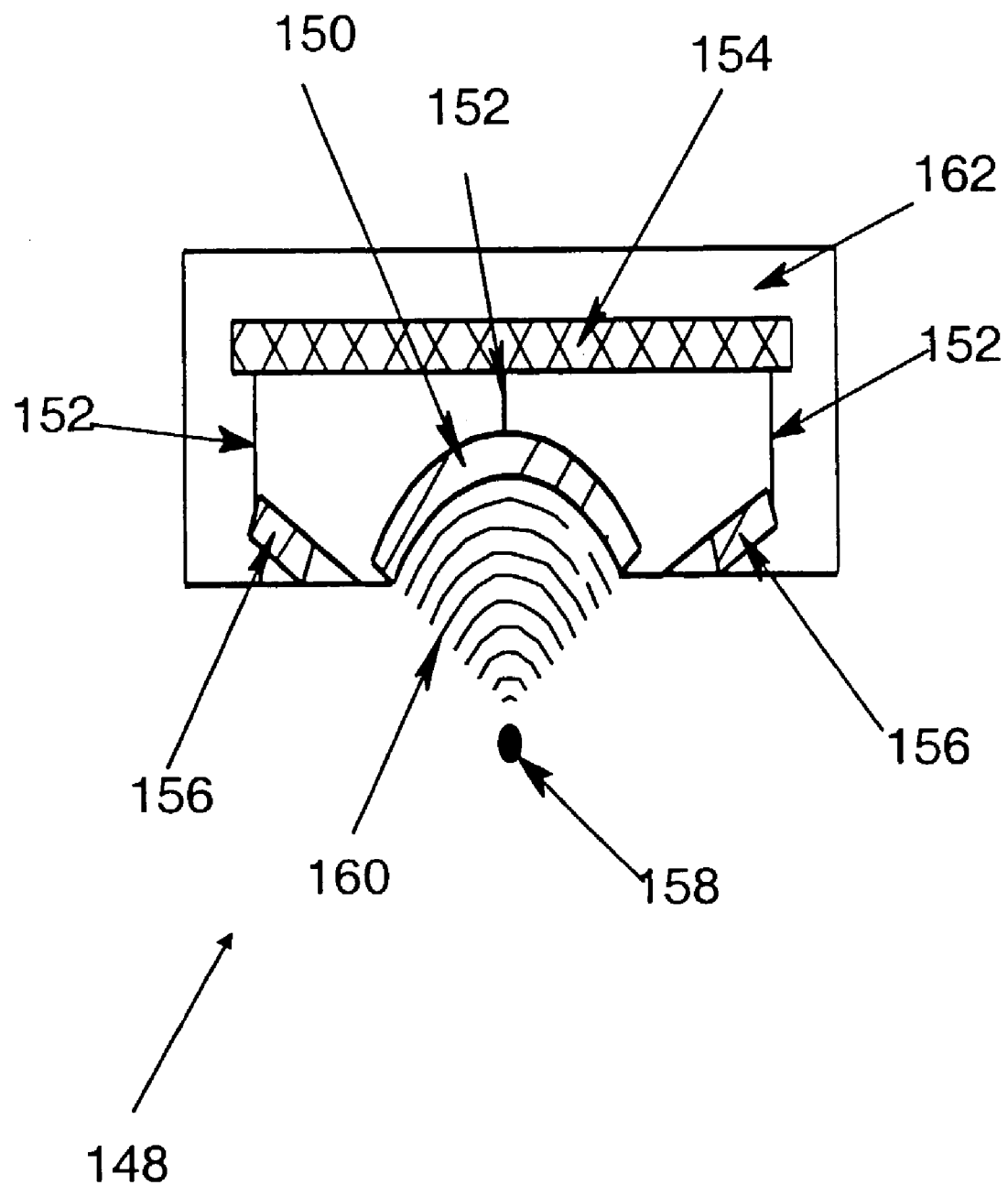
FIG. 6 shows a detail of the sensor package shown in FIGS. 4 and 5, according to a preferred embodiment of the invention.

FIG. 6 shows a detail of the sensor package shown in FIGS. 4 and 5, according to a preferred embodiment of the invention. Sensor package 148 thus corresponds to the thermophysical property package 130 shown in FIG. 5, or the bubble detection and formation system 124 shown in FIG. 4. Sensor package 148 comprises an acoustic transducer 150 that is preferably of concave shape focused at a point 158 away from the wall of the vessel or tubing. Acoustic transducer 150 is preferably operates in the ultrasonic range, such as around 40 kHz, however frequencies as low as 1 kHz or as high as 50 kHz could be suitable for some applications. Bubbles generated by transducer 150 could be detected with bubble detection transducers 156, which are preferably located up and down stream of point 158. However, according to a preferred embodiment, the same transducer used to form the bubbles could be used for bubble detection. According to this embodiment, transducer 150 would be used for detecting the presence of bubbles. Transducers 150 and 156 are connected to electronics and processing system 154 by cables 152. The active parts of the mechanism are housed in a container 162.

Advantageously, the arrangement shown in FIG. 6 can also be used for acoustic wave time-of-flight and impedance measurements to provide flow rate, sound speed, viscosity and density. The required fluid speed of sound could be determined from time of flight measurements between transducers 156 for example or from ancillary measurements with other instrumentation.

Figure 7:
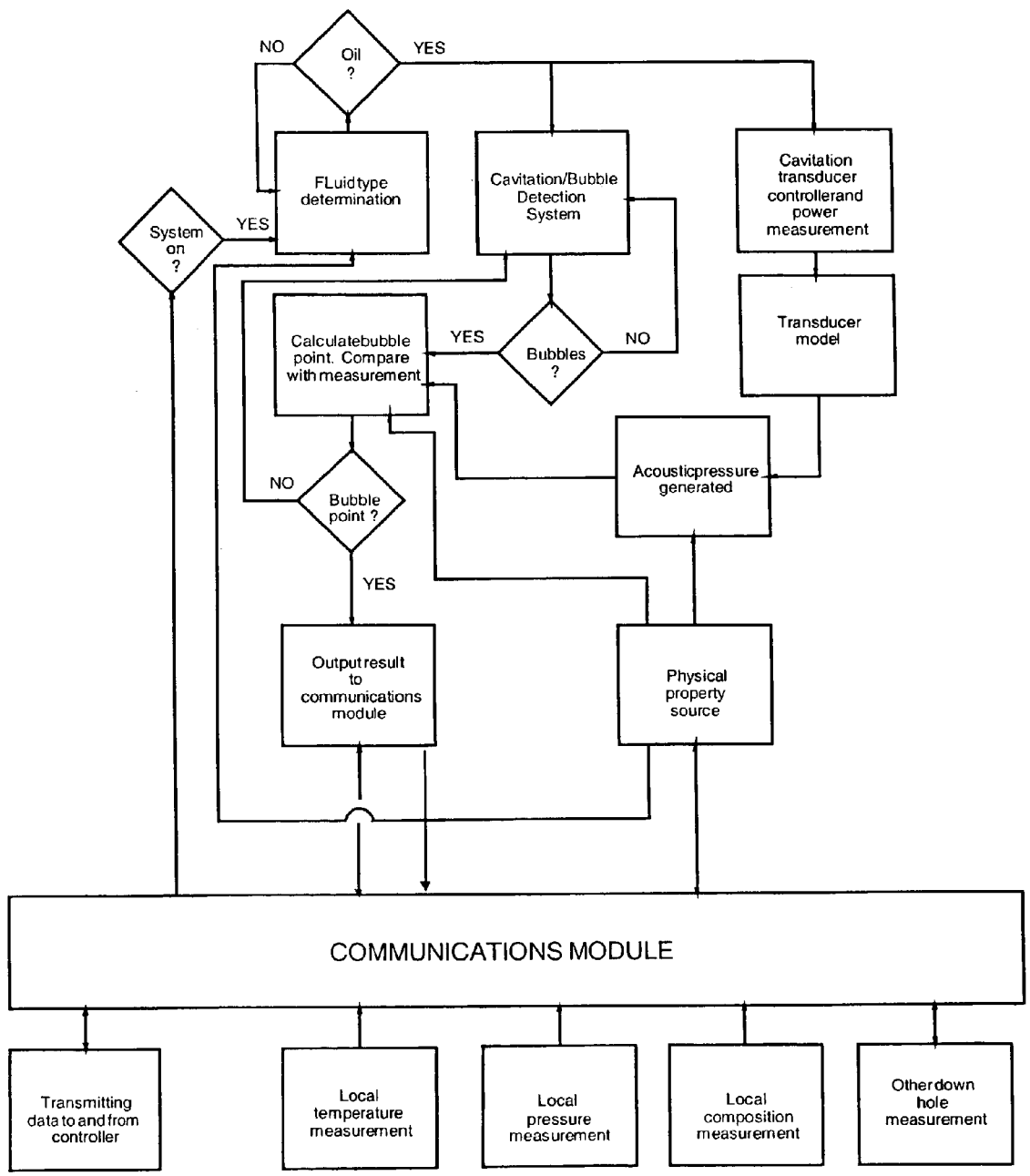
FIG. 7 shows the detail of an electronics module used to control the bubble point detection system, according to a preferred embodiment of the invention.

FIG. 7 shows the detail of an electronics module used to control the bubble point detection system, according to a preferred embodiment of the invention. The logic of the bubble point measurement electronics and software is shown, which includes error checking, ancillary measurements, and communications as shown.

Figure 8:
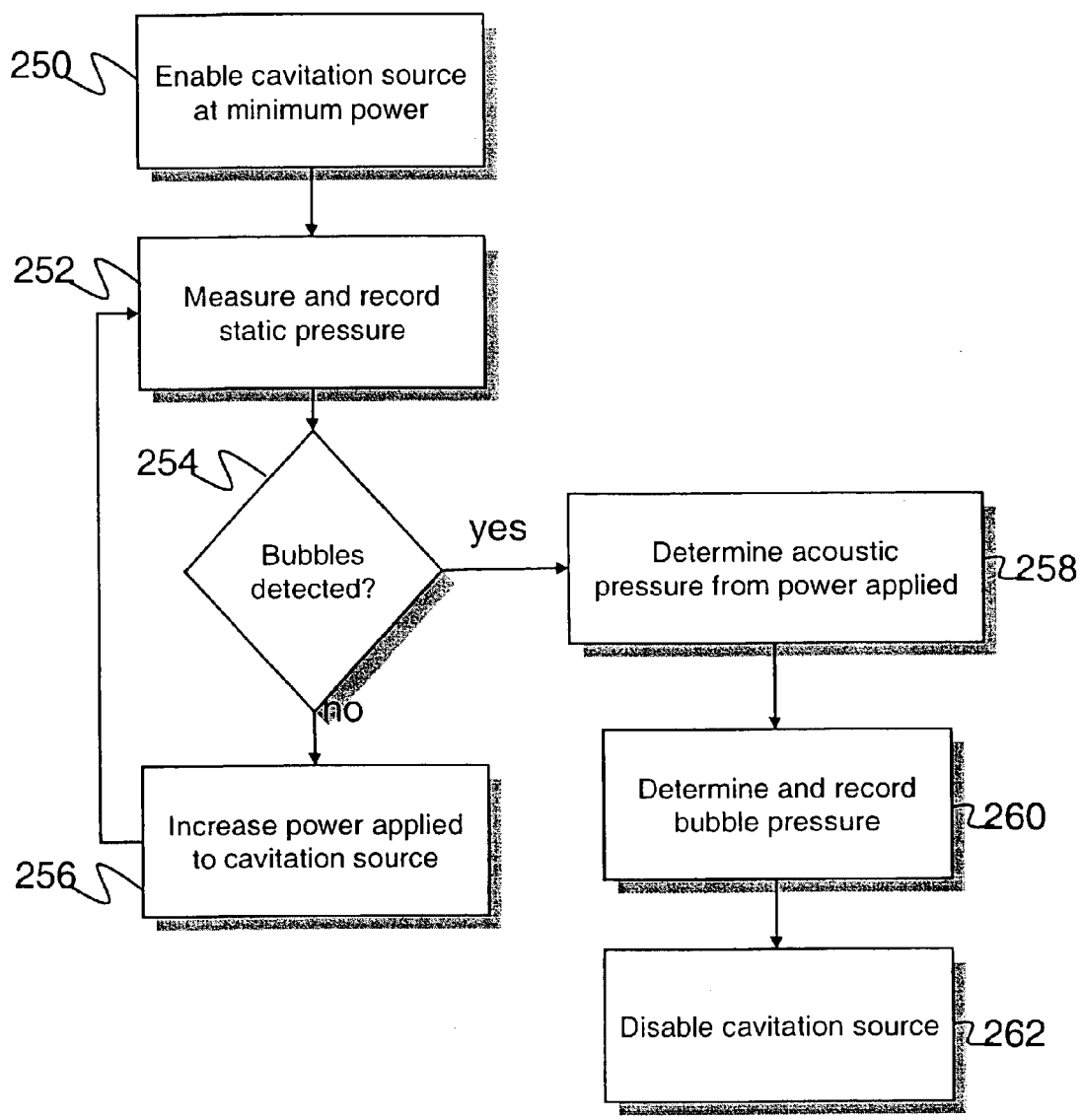
FIG. 8 is a flow chart of the steps used in detecting bubbles formed by cavitation, according to a preferred embodiment of the invention.

FIG. 8 is a flow chart of the steps used in a batch mode of determining the bubble point pressure, according to a preferred embodiment. In step 250 the cavitation source is enabled at minimum power. The cavitation source can be of the type and configuration as transducer 150 shown in FIG. 6. In step 252 the static pressure is measured and recorded. In step 254 the presence of bubbles are detected. The preferred method of detecting the presence of bubble is described in further detail below. If bubbles are not detected, the power applied to the cavitation source is increased in step 256, and steps 252 and 254 are repeated. Optionally, step 252 can be omitted after increasing the power, in which case the loop back arrow from step 256 on FIG. 8 would instead point to step 254.

When the presence of bubbles is detected, the acoustic pressure is determined from the power applied to the acoustic transducer, step 258. The preferred method of making this determination is using finite difference methods to solve the equations for acoustic propagation as described above. In step 260 the bubble pressure is determined by subtracting the acoustic pressure determined in step 258 from the static pressure measured in step 250. Finally, in step 262, the cavitation source is disabled. Alternatively, the bubble point pressure can be determined using a continuous rather than batch mode. In the case of continuous mode bubble point sensing, the algorithm shown in FIG. 8 would simply loop back from step 260 to either step 252 or 254.

The method described in FIG. 8 thus has the advantage over other methods in that it does not require the enclosure of a sample of fluid in a chamber, and does not require that the volume be changed using mechanical means such as a plunger, piston, or the like. Such mechanical means are more prone to wear, and other reliability problems, are therefore not as well suited to permanent or semi-permanent installation as is this embodiment of the present invention.

The preferred method of detecting the presence of bubbles will now be describe in further detail. Preferably, bubbles are sensed at the location of the ultrasonic transducer used for cavitation. The acoustic impedance sensed by the ultrasonic transducer is extremely sensitive to the presence of bubbles, so bubbles can be produced and sensed at the same site, with very high reliability. The pressure of the fluid at which bubbles are first generated by the ultrasonic transducer is measured by a precision gauge, such as the Schlumberger CQG quartz pressure gauge.

The acoustic impedance of a material is defined as the product of its mass density and sound speed. In one implementation of the invention, the acoustic impedance of the transducer is approximately matched to the acoustic impedance of the fluid, in the absence of bubbles. At the first appearance of a bubble, both the density and the sound speed of the fluid decrease. The transducer and fluid are no longer impedance matched acoustically. Under this condition, the electrical impedance of the transducer increases.

Figure 9:
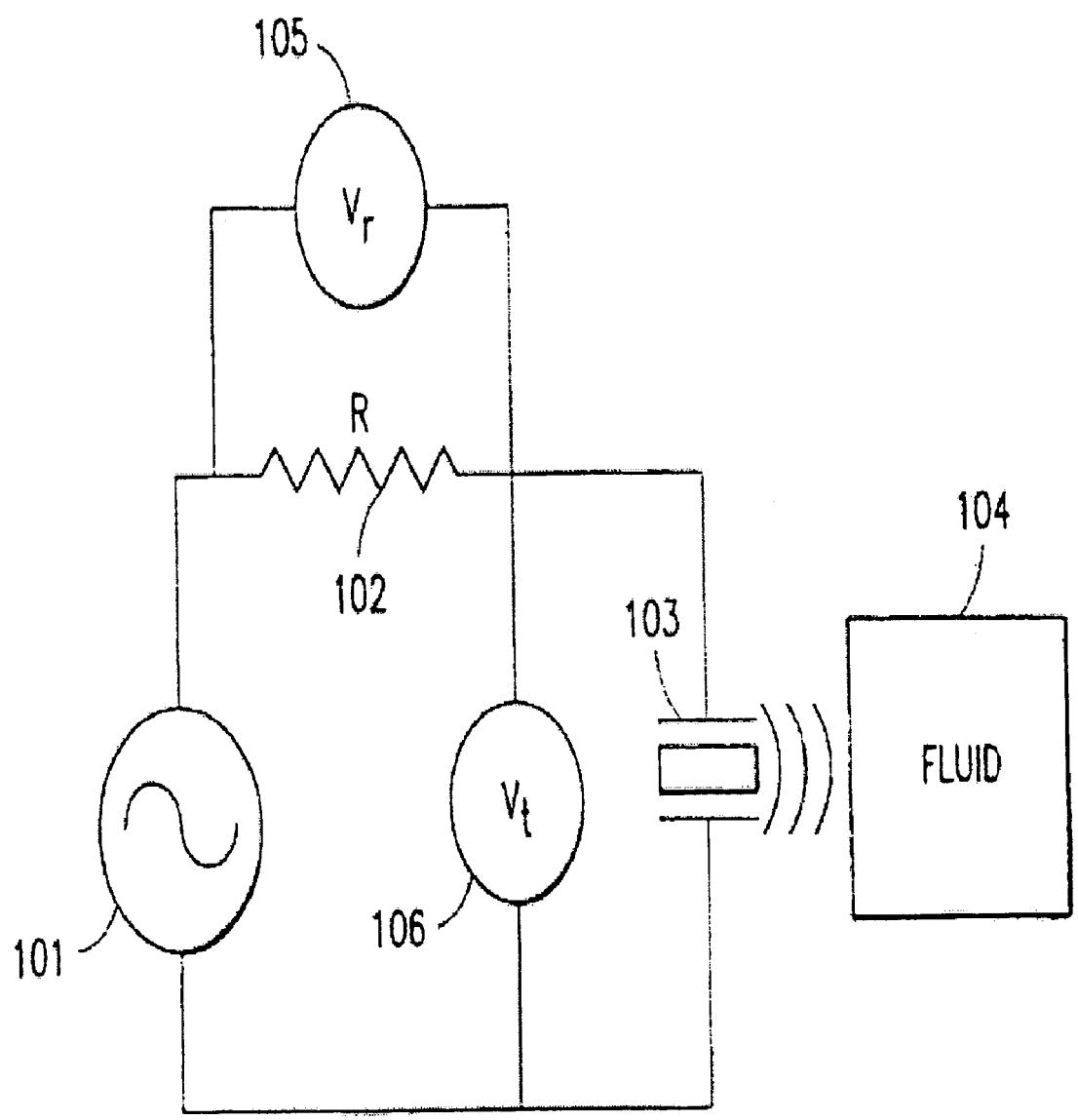
FIG. 9 is a schematic diagram of an electrical circuit for monitoring transducer impedance, according to a preferred embodiment of the invention.

Referring to FIG. 9, there is shown a simple electrical circuit used to monitor the electrical impedance of the transducer. An electronic oscillator 101 drives alternating current through a resistor 102 (having fixed resistance, R) and an acoustic transducer 103. Transducer 103 radiates sound energy into fluid 104.

The current in the circuit, I, is monitored by using a high-impedance voltmeter 105 to measure the voltage, Vr, across resistor 102. Ohm's Law states that $I=V_r/R$.

The voltage across transducer 103, Vt, is monitored by a second voltmeter 106. The electrical impedance of the transducer 103 is $Z=V_t/I=(V_t/V_r)R$.

When the acoustic impedance of the transducer is matched to the acoustic impedance of the fluid, in the absence of bubbles, the voltage across the transducer is relatively low; the current is relatively high. Thus, the electrical impedance of the transducer is relatively low.

When the acoustic impedances of transducer and fluid are mismatched, however, in the presence of bubbles, the voltage across the transducer increases and the current decreases, increasing the electrical impedance.

Thus far, the bubble point determination method of FIG. 8 and the sensors of FIGS. 4, 5, and 6 have been described in connection with a real-time process controller for a well. However other preferred embodiments for the sensors and detection methods exist.

Figure 10:
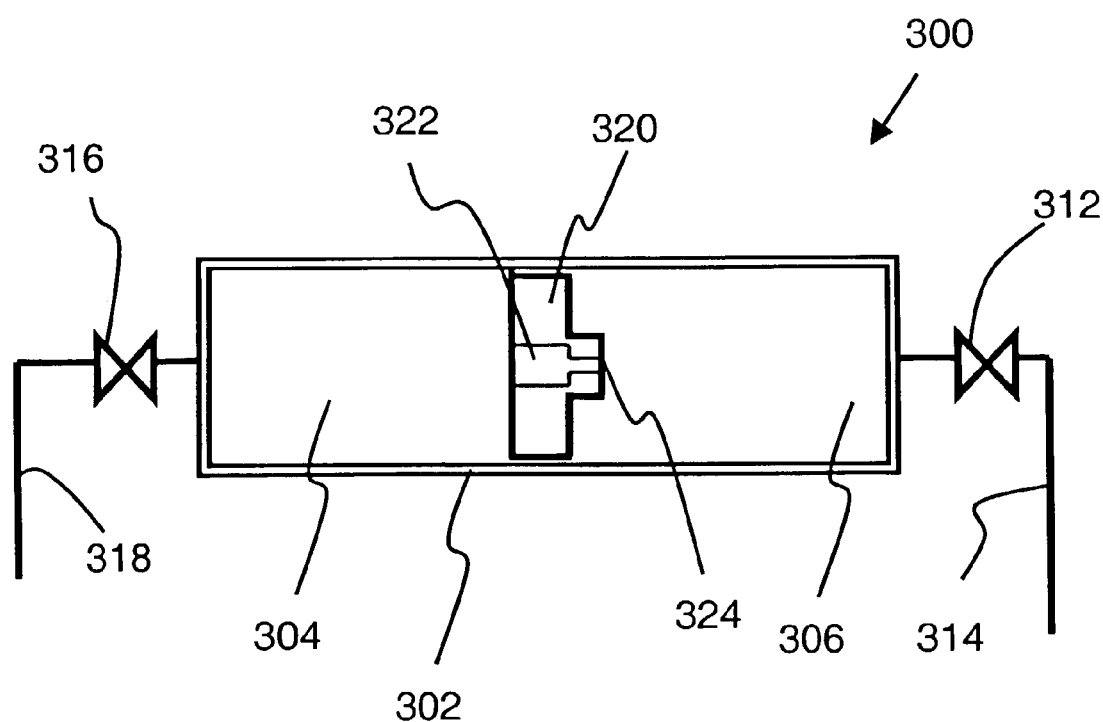
FIG. 10, shows a schematic diagram of an apparatus for measuring the phase characteristics in accordance with an alternative embodiment of the invention.

FIG. 10, shows a schematic diagram of an apparatus for measuring the phase characteristics in accordance with an alternative preferred embodiment of the invention. According to this embodiment, the phase characteristics, such as bubble point pressure, can be determined for a production fluid while in a sample bottle 300. Sample bottle 300 comprises a sealed container 302, preferably made of steel, sample fluid inlet 314, hydraulic fluid inlet 318, and a movable piston 320. Hydraulic fluid can be pumped through valve 316 into the bottle at region 304 on the left of the piston. The sample fluid can enter the bottle through valve 312 and into the region 306 on the right side of the piston. By controlling the pressure of the hydraulic fluid in region 304, the volume and thus pressure of the sample fluid can be altered and maintained. Typically, a sample of production fluid taken downhole can be placed into the bottle and the formation pressure can be maintained in the bottle using the hydraulic system and the piston.

According to the invention, piston 320 includes a phase transition detector 322. The detector 322 preferably operates as described above, using an acoustic transducer to both generate and detect the presence of bubbles in the fluid sample. Preferably, the acoustic energy from the transducer 322 is emitted from a portion 324 that protrudes from piston 320 into the sample region 306. The phase transition detector is preferably used to detect the bubble point pressure. However, it is believed that a similar arrangement could be used to detect the dew point pressure. Additionally, the sample bottle can be used either downhole, as part of a downhole sampling tool, or on the surface.

When detecting bubble point pressure, the sample fluid is inserted from inlet line 314 through valve 312. If there is a great difference between the pressure of the fluid and the expected bubble point pressure, the pressure can be altered using the hydraulic system so as to bring the pressure of the fluid to within the range of the bubble point pressure. Preferably the pressure of the fluid is within the range of pressure generating capabilities of the acoustic transducer. The steps illustrated in FIG. 8 then can be used to detect the bubble point pressure either in a burst or continuous mode.

Figure 11:
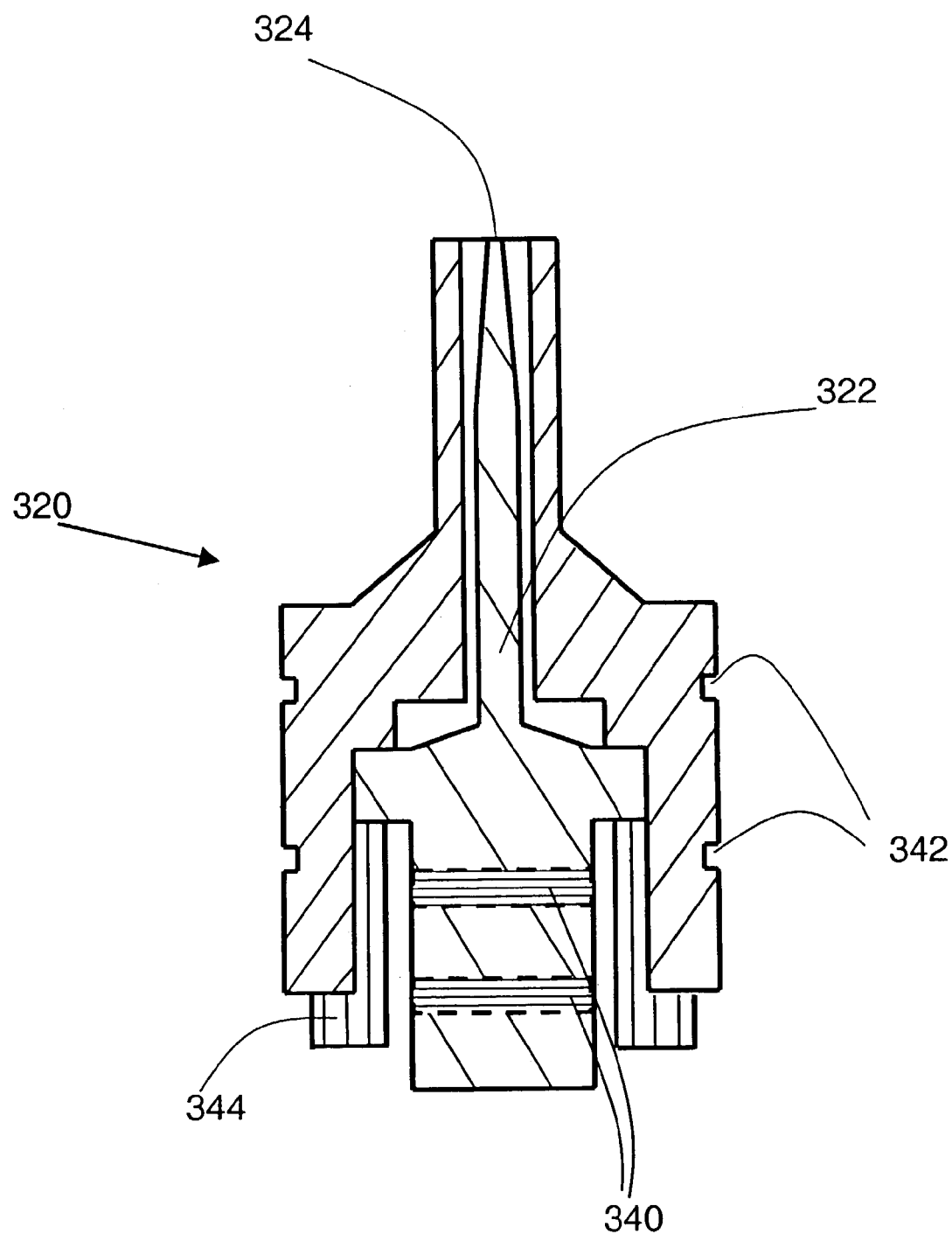
FIG. 11, shows a cross section of a piston for use in the apparatus of FIG. 10, according to an embodiment of the invention.

FIG. 11, shows a cross section of piston 320 for use in the apparatus of FIG. 10, according to an embodiment of the invention. Horn transducer 322 positioned inside piston 320. The acoustic energy is directed from the tip of the transducer, at location 324. Clamping device 322 is used to hold the transducer 322 in place. Piezo electric crystals 340 are shown which are used in generating the acoustic energy. Additionally, grooves 342 are provided to accept o-ring seals for piston 320.

While preferred embodiments of the invention have been described, the descriptions are merely illustrative and are not intended to limit the present invention. For example, although much of the description herein is directed to bubble point determination, the methods described are believed to be applicable to dew point determination.

What is claimed is:

1. A control system for a hydrocarbon well comprising:
    a control valve system configured to control the flow of fluid being produced by the well;
    a real time sensor located downhole configured and adapted to make real time measurements of phase characteristics of the fluid, wherein the phase characteristics measured by the sensor comprise bubble point pressure; and
    a controller in communication with said control valve system and said sensor adapted and configured to use measurements made by said sensor to control the control valve system so as to reduce the risk of undesirable phase transitions in the fluid.

2. The control system of claim 1 wherein the real time sensor is installed permanently downhole in the well.

3. The control system of claim 1 wherein the real time sensor is installed semipermanently downhole in the well.

4. The control system of claim 1 wherein the sensor causes cavitation and the formation of bubbles using at least one of the methods including passive emissions, transmission, reflection, sound speed, sound attenuation, optical, Doppler, back-scattering, holography, microscopy, and Mie scattering.

5. The control system of claim 1 wherein the sensor comprises an acoustic transducer configured to emit acoustic energy into the fluid at a level which causes a phase transition in the fluid.

6. The control system of claim 5 wherein said controller is in communication with said acoustic transducer, and said controller is adapted and configured to determine the level of acoustic energy emitted into the fluid, and to determine the pressure associated with a phase transition at least in part by using the level of emitted acoustic energy.

7. The system of claim 5 wherein the determination of the pressure associated with the phase transition does not rely on mechanical means to substantially alter the volume of a sample of the fluid.

8. The system of claim 5 wherein the phase transition is the bubble point and the pressure associated with the phase transition is the bubble point pressure.

9. The system of claim 5 wherein the phase transition is the dew point and the pressure associated with the phase transition is the dew point pressure.

10. The system of claim 8 wherein the acoustic energy is emitted by the acoustic transducer at a frequency less than 1 MHz.

11. The system of claim 10 wherein the acoustic energy is emitted by the acoustic transducer at a frequency between about 1 and about 50 kHz.

12. The system of claim 11 wherein the pressure associated with the phase transition is determined by sensing variations in impedance of the acoustic transducer which indicate the presence of bubbles in said fluid.

* * * * *